Aug. 22, 1961 H. C. SWIM Plant Pat. 2,078
ROSE PLANT
Filed Oct. 24, 1960
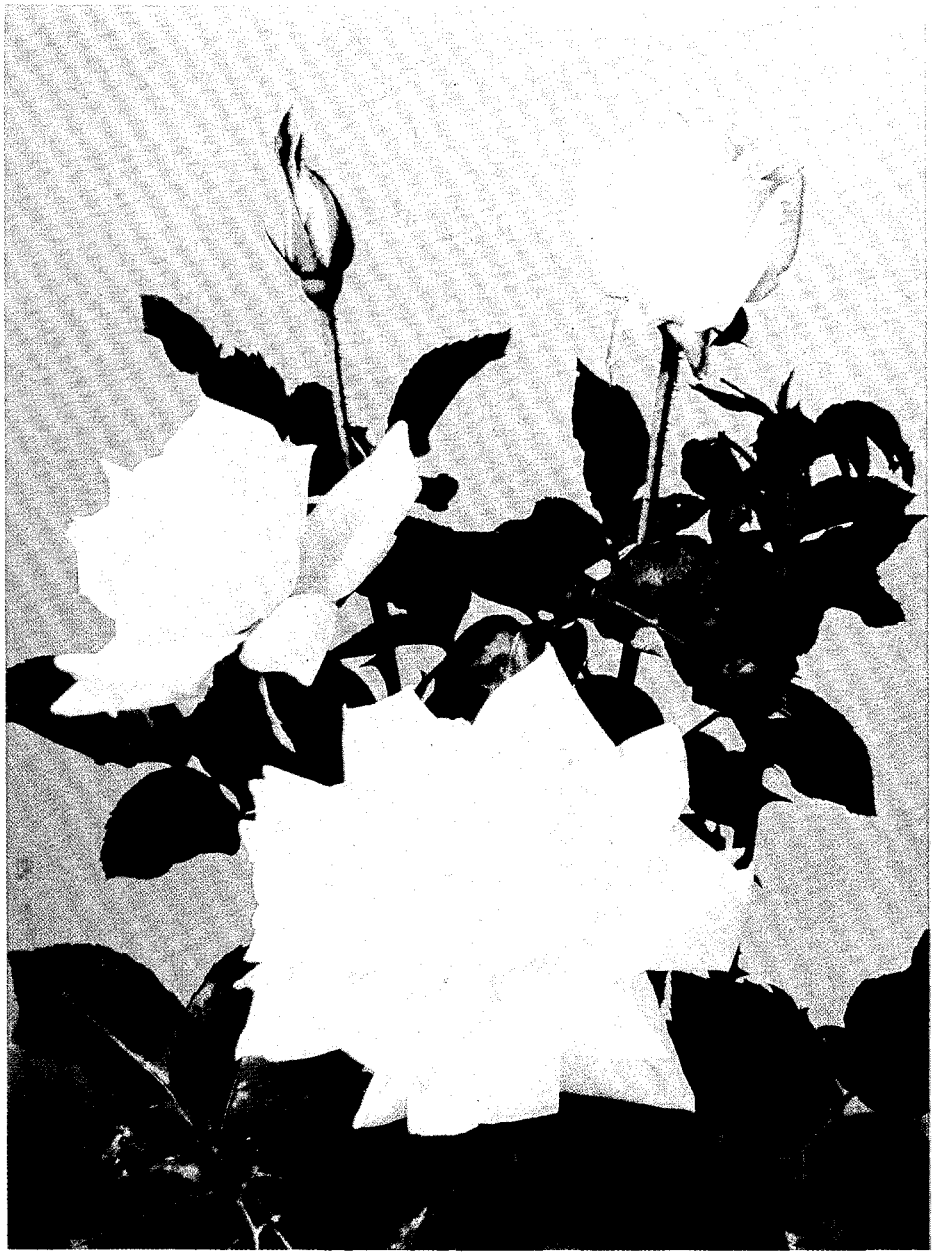
Inventor.
H. C. Swim
By: Robb & Robb
Attorneys.

United States Patent Office

Plant Pat. 2,078
Patented Aug. 22, 1961

2,078
ROSE PLANT

Herbert C. Swim, Ontario, Calif., assignor to Armstrong Nurseries, Inc., Ontario, Calif., a corporation of California Filed Oct. 24, 1960, Ser. No. 64,686
1 Claim. (Cl. 47—61)

The present invention relates to a new and distinct variety of rose plant of the hybrid tea class, which was originated by me by crossing the variety "Buccaneer" (Plant Patent No. 1,119) with the variety "Lemon Chiffon" (Plant Patent No. 1,241).

The general objective of this breeding was to produce an improved hybrid tea rose variety which bears flowers of a deep yellow color, with particular emphasis upon improvement of the vigor and of the foliage of the plant, attainment of longer flower stems, with the flowers borne singly and having a good bud and open flower form and the flowers being characterized by a non-fading deep yellow color as far as possible. This objective was achieved, along with other desirable improvements, as evidenced by the following unique combinations which are outstanding in the new variety, and which distinguish it from its parents, as well as from all other varieties of which I am aware:

(1) A vigorous, upright-spreading and well-branched plant habit that is generally more vigorous than any known truly deep and relatively unfading yellow hybrid tea variety;

(2) Attractive dark green foliage;

(3) A habit of generally bearing the flowers on relatively long, single stems;

(4) Moderately double flowers having a good urn-shaped bud form and an attractive open flower form which is generally better than other truly deep, relatively unfading yellow hybrid tea flowers;

(5) A deep and relatively unfading yellow flower color that is fully the equal or better than any other known yellow rose; and (6) Excellent petal substance, with attendant long lasting flower qualities.

In comparison with its seed parent, "Buccaneer," my new variety is less vigorous; its habit is more compact and more branched; the flowers are generally borne on single stems, whereas the variety "Buccaneer" is rather tall, leggy and only moderately branched in its habit of growth, and usually bears flowers in small clusters; and the bud form of my new variety is more urn-shaped, generally speaking, than that of "Buccaneer."

As compared with its pollen parent, "Lemon Chiffon," my new variety is considerably more vigorous when grown under the same conditions; and has longer and stronger stems, generally speaking, which may be attributed to its increased vigor; the stipitate glands and prickles on the peduncle are somewhat larger and more numerous; the thorne, on the average, tend to be more curved downwardly; and the petalage is usually less on the average than that of "Lemon Chiffon."

Asexual reproduction of my new variety by budding, as performed at Ontario, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated:

Type: Bush; outdoor; seedling; for cut flowers and for garden decoration.

Class: Hybrid tea.

Breeding: Seedling.

*Seed parent.*—"Buccaneer."

*Pollen parent.*—"Lemon Chiffon."

Propagation: Holds its distinguishing characteristics through succeeding propagations by budding.

*Flower*

Locality where grown and observed: Ontario, California.

Flowers borne: Usually singly, but sometimes 2 to 3 to stem; on strong stems varying in length from medium to long.

Quantity of bloom: Abundant, outdoors.

Continuity: Nearly continuous during growing season.

Fragrance: Slight.

Bud:

*Peduncle.*—Average length; from average to heavy caliper; erect; usually has relatively many stipitate glands and from few to numerous small prickles. Color—near Absinthe Green, Plate XXXI (Ridgway), overlaid with near Light Yellowish Olive, Plate XXX (Ridgway), on side exposed to sun.

*Before calyx breaks.*—Size—medium. Form—medium length; ovoid.

*As calyx breaks.*—Color—between Canary Yellow, Plate 2, page 2 (Wilson), and Aureolin, Plate 3, page 3 (Wilson), overlaid with near Tangerine Orange, Plate 9/2, page 9 (Wilson), on areas exposed longer to the sun.

*Sepals.*—Inner surface—with fine, woolly tomentum. Outer surface—usually with from few to several small stipitate glands. Alternate margins—lined with fine, woolly tomentum. Other margins—with numerous small sipitate glands and several foliaceous parts ranging in size from small to medium. Foliaceous parts—often extending beyond the tip of the bud equal to ¼ to ½ its length.

*As first petal opens.*—Size—average. Form—medium length; from ovoid to urn-shaped. Color: outside—between Aureolin, Plate 3/1, page 3 (Wilson), and Lemon Yellow, Plate 4/1, page 4 (Wilson); inside—between Canary Yellow, plate 2/1, page 2 (Wilson), and Aureolin, Plate 3/1, page 3 (Wilson).

*Opening.*—Opens up well; is not retarded or prevented from opening by cold, hot, wet or dry weather.

Bloom:

*Size (when fully open).*—From average to large; from 3½ inches to 5 inches.

*Petalage.*—Double; from 22 to 28 petals, plus 4 to 8 petaloids; arranged irregularly.

*Form.*—High-centered at first, but becoming from cupped to high-centered; petals being at first somewhat tightly cupped, with tips reflexed outward, but later becoming from loosely flat to cupped, with tips reflexed outward at maturity; outside and intermediate petals of newly opened flower usually slightly reflexed outward along edges of petals and at apex; outside and intermediate petals of 3-days open flower usually reflexed strongly outward along edges of petals and at apex.

Petals:

*Texture.*—Medium thickness. Inside—satiny. Outside—satiny.

*Shape.*—Outside—between round and broadly obovate, with apex flat and usually with from 1 to 3 notches. Intermediate—broadly obovate, with apex rounded, and sometimes with 1 or 2 notches. Inside—obovate, with apex rounded, and sometimes with 1 or 2 notches.

This description of a newly opened flower was made from a rose grown outdoors in the month of September at Ontario, California.

*Color.*—Outer petal: outside surface—near Aureolin, Plate 3/2, page 3 (Wilson), blending with near Aureolin, Plate 3, page 3 (Wilson), toward base of petal; inside surface—between Canary Yellow, Plate 2/3, page 2 (Wilson), and Lemon Yellow, Plate 4/3, page 4 (Wilson), blending with near Canary Yellow, Plate 2/1, page 2 (Wilson) toward base of petal. Intermediate petal: outside surface—between Aureolin, Plate 3/1, page 3 (Wilson), and Lemon Yellow, Plate 4/1, page 4 (Wilson); inside surface—between Canary Yellow, Plate 2/1, page 2 (Wilson), and Aureolin, Plate 3/1, page 3 (Wilson). Inner petal: outside surface—near Aureolin, Plate 3/1, page 3 (Wilson); inside surface—between Canary Yellow, Plate 2/1, page 2 (Wilson), and Aureolin, Plate 3/1, page 3 (Wilson).

This description was made from a rose that was open for 3 days outdoors in the month of September, at Ontario, California:

*Color.*—Outer petal: outside surface—near Mimosa Yellow, Plate 602/1, page 143 (Wilson), blending ing with near Canary Yellow, Plate 2/2, page 2 (Wilson), toward base of petal; inside surface—near Empire Yellow, Plate 603/1, page 66 (Wilson), blending with near Canary Yellow, Plate 2/1, page 2 (Wilson), toward base of petal. Inner petal: outside surface—between Sulfur Yellow, Plate 1/3, page 1 (Wilson), and Canary Yellow, Plate 2/3, page 2 (Wilson), blending with near Sulfur Yellow, Plate 1/1, page 1 (Wilson), toward base of petal; inside surface—near Primrose Yellow, Plate 601/2, page 65 (Wilson), blending with near Canary Yellow, Plate 2/2, page 2 (Wilson), toward base of petal.

*General color effect.*—Newly opened flower—between Canary Yellow, Plate2 /3, page 2 (Wilson), and Lemon Yellow, Plate 4/1, page 4 (Wilson). 3-days open—between Primrose Yellow, Plate 601/2, page 65 (Wilson), and Empire Yellow, Plate 603/1, page 66 (Wilson).

*Behavior.*—Drop off cleanly; not particularly affected by cold, hot, wet or dry weather.

*Flower longevity.*—On bush in garden—4 or 5 days in June. Cut roses grown outdoors and kept at living-room temperatures—5 or 6 days in June.

*Reproductive organs*

Stamens: Average number; arranged regularly about pistils; a few mixed with petaloids.

Filaments: From short to medium length; from 5 to 15 mm. in length; most with anthers. Color—between Lemon Yellow, Plate 4/2, page 4 (Wilson), and Cadmium Orange, Plate 8/1, page 8 (Wilson).

Anthers: From small to medium size; all open approximately at once. Color: upper side—margins near Cadmium Orange, Plate 8, page 8 (Wilson), with remainder near Lemon Yellow, Plate 4/2, page 4 (Wilson); under side—margins near Cadmium Orange, Plate 8, page 8 (Wilson), with remainder near Lemon Yellow, Plate 4/2, page 4 (Wilson).

Pollen: Normally abundant. Color—near Orpiment Orange, Plate 10/1, page 10 (Wilson).

Pistils: Average number (approximately 60).

Styles: Uneven length; from short to average length (from 3–10 mm.); thin; bunched. Color—near Dresden Yellow, Plate 64/2, page 64 (Wilson); sometimes upper ⅓ to ¼ of styles overlaid with near Rose Madder, Plate 23/2, page 23 (Wilson).

Stigma: Color—near Empire Yellow, Plate 603, page 66 (Wilson).

Ovaries: Usually all enclosed in calyx.

Hips: None observed at Ontario, California.

Sepals: None observed at Ontario, California.

Seeds: None observed at Ontaria, California.

*Plant*

Foliage:

*Leaves.*—Compound of usually 3 to 7 leaflets; from normal quantity to abundant; from medium size to large; leathery; semi-glossy.

*Leaflets.*—Shape—oval, with apex acute. Base—from round to obtuse. Margin—simply serrate.

*Color.*—Mature: upper surface—between Forest Green, Plate XVII (Ridgway), and Dark Dull Yellow-Green, Plate XXXII (Ridgway); under surface—near Chromium Green, Plate XXXII (Ridgway). Young: upper surface—near Deep Olive, Plate XL (Ridgway), overlaid with near Dark Corinthian Purple, Plate XXXVIII (Ridgway), near edge of leaflets; under surface—near Dark Corinthian Purple, Plate XXXVIII (Ridgway).

*Rachis (the supporting stem of the compound leaf).*—Average size. Upper side—grooved, with from few to several stipitate glands on edges. Under side—smooth, with from none to few stipitate glands and none to few small prickles.

*Stipules.*—From short to medium length; narrow; with short points turning out at an angle of more or less than 45°.

*Disease resistance.*—Average resistance to mildew as compared with other varieties grown under comparable cultural conditions at Ontario, California.

Growth:

*Habit.*—Upright-spreading; much-branched.

*Growth.*—From moderate to free.

*Canes.*—Medium caliper.

*Main stems.*—Color—near Deep Chrysolite Green, PlateXXXI (Ridgway). Large prickles—from a few to several; from medium length to long; straight; with narrow base of medium length; color—near Cinnamon, Plate XXIX (Ridgway). Small prickles—few; color—near Cinnamon, Plate XXIX (Ridgway). Hairs—none.

*Branches.*—Color—near Light Elm Green, Plate XVII (Ridgway). Large prickles—from few to several; medium length; almost straight; with narrow base of medium length; color—near Pecan Brown, Plate XXVIII (Ridgway). Small prickles—from few to several; color—near Pecan Brown, Plate XXVIII (Ridgway). Hairs—none.

*New shoots.*—Color—near Apple Green, Plate XVII (Ridgway), overlaid with near Sorghum Brown, Plate XXXIX (Ridgway). Large prickles—from few to several; from short to medium length; hooked slightly downward; with narrow base of medium length; color—near Terra Cotta, Plate XXVIII (Ridgway). Small prickles—from few to several; color—near Terra Cotta, Plate XXVIII (Ridgway). Hairs—none.

I claim:

A new and distinct variety of rose plant of the hybrid tea class, substantially as herein shown and described, characterized particularly as to novelty by the unique combination of a vigorous, upright-spreading, well-branched habit of growth, attractive dark green foliage, a habit of generally bearing flowers on relatively long, single stems, moderately double flowers having a good urn-shaped bud form and attractive open flower form, a deep yellow and relatively non-fading color tonality of the flowers, and an excellent petal substance, with attendant long-lasting flower qualities.

No references cited.